United States Patent [19]

Retz

[11] Patent Number: 4,660,948

[45] Date of Patent: Apr. 28, 1987

[54] EYE CHART

[76] Inventor: Philip Retz, 1783 Lanier Pl. NW., Washington, D.C. 20009

[21] Appl. No.: 773,512

[22] Filed: Sep. 5, 1985

Related U.S. Application Data

[63] Continuation of Ser. No. 580,211, Feb. 15, 1984, abandoned.

[51] Int. Cl.⁴ ............................................. A61B 3/04
[52] U.S. Cl. .................................. 351/239; 351/200; 351/203
[58] Field of Search ............... 351/200, 201, 202, 203, 351/239, 240–243

[56] References Cited

U.S. PATENT DOCUMENTS

| | | |
|---|---|---|
| 978,277 | 12/1910 | Cross . |
| 1,412,902 | 4/1922 | Tallman . |
| 1,879,833 | 9/1932 | Tillyer . |
| 1,999,054 | 4/1935 | Lee . |
| 2,352,500 | 6/1944 | Shepard . |
| 2,385,992 | 10/1945 | Jobe . |
| 2,463,813 | 3/1949 | Shepard . |
| 2,723,466 | 11/1955 | Ott . |
| 2,747,458 | 5/1956 | Richards ........................ 351/240 |
| 3,011,394 | 12/1961 | Sherman . |
| 4,257,690 | 3/1981 | Howland . |

OTHER PUBLICATIONS

Laurence et al; Visual Optics and Sight Seeing, 1936, p. 243.
Coulden; Versatility in Subjective Refraction; The Optician, vol. 153; Mar. 1967, pp. 291–293.

Primary Examiner—Rodney B. Bovernick
Assistant Examiner—P. Dzierzynski
Attorney, Agent, or Firm—Saidman, Sterne, Kessler & Goldstein

[57] ABSTRACT

An eye chart for use in a treatment program that includes eye exercises comprises a peripheral line defining a geometric shape and a pair of intersecting lines within the area defined by the peripheral line. Spool-shaped images are superimposed on the peripheral line in a predetermined pattern and one of the intersected lines includes an intermediate wavy portion. Numerals of desired sizes are located at various positions on the chart. The invention also encompasses several eye exercise methods utilizing the chart.

20 Claims, 1 Drawing Figure

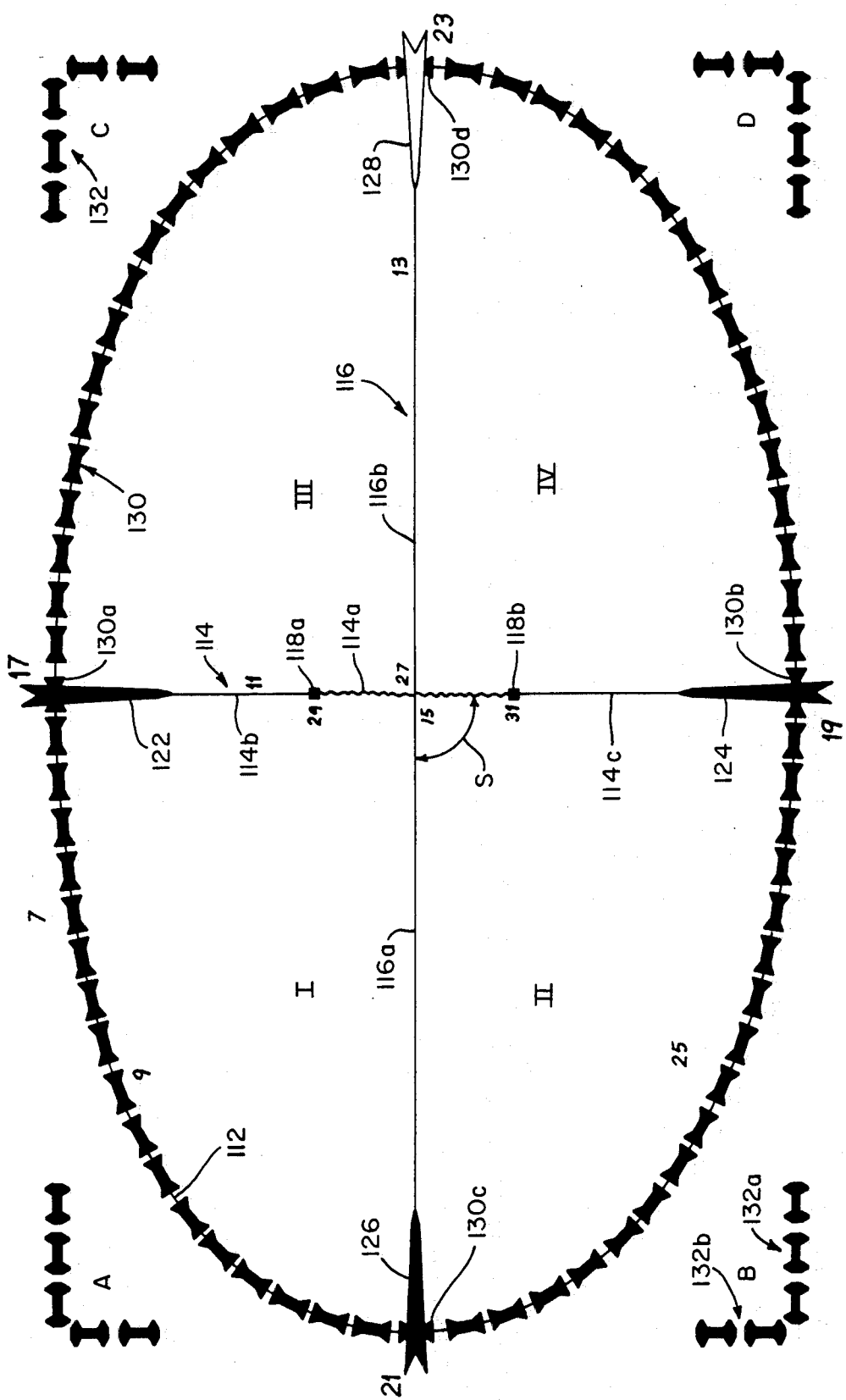

EYE CHART

This application is a continuation, of application Ser. No. 580,211, filed Feb. 15, 1984, now abandoned.

BACKGROUND OF THE INVENTION

1. Field of the Invention

The invention relates to eye charts, and method for using the eye chart for correcting certain visual deficiencies. More particularly, the invention relates to a new and different eye chart and method of using it to correct for amblyopia and diplopia.

2. Description of the Related Art

There have been many eye charts designed for testing visual acuity. Some charts incorporate various characters or figures printed on a contrasting background. Others incorporate opaque figures printed on a transparency for projection onto a screen. U.S. Pat. Nos. 2,385,992; 3,011,394; and 4,257,690 disclose examples of various kinds of eye testing charts that have been available up to now.

A feature common to previously known charts is that they are designed only to test the condition of the eyes. None are designed for treating existing visual deficiencies.

Amblyopia is a condition in which the eyes see with differing degrees of clarity or sharpness. The better eye tends to do all the work while the weak eye does little or none. The weak eye may also wander. Diplopia is a condition in which a person sees double images when viewing small pictures or fine print, such as newspaper print. This is due to unequal action of the eye muscles. People who write or draw extensively may develop this problem because the hand which is writing or drawing blocks the work from the view of the corresponding eye. The eye whose view is blocked is not used, and the muscles become weak.

To overcome and correct these conditions, it is important for an individual to develop greater control over the eye muscles. Consequently, it would be desirable to have a simple, yet effective means and method for exercising the eyes and the muscles associated with the eyes, to help overcome amblyopia and diplopia.

The eye chart and method in accordance with the present invention may be advantageously used to rehabilitate the vision of a person suffering from certain conditions, such as amblyopia or diplopia. Use of the inventive chart in accordance with the described methods increases muscular strength and improves control of the muscles associated with the eye. A chart in accordance with the present invention is very inexpensive, and the inventive method may easily be practiced by a lone individual, without additional aid or equipment. An optometrist can use the chart in conjunction with other equipment to treat eye muscle problems.

It is an object of the present invention to provide means for aiding in the treatment of certain visual impairments.

It is an object of this invention to provide means to treat amblyopia and diplopia.

It is another object of this invention to provide a method for helping to correct certain temporary eye problems.

It is an object of this invention to provide a method which can be easily practiced by an individual without the aid of others and without complex or expensive equipment.

SUMMARY OF THE INVENTION

The present invention includes a chart for treating amblyopia and diplopia. The chart preferably has an eggplant oval area or shape with built-in nuances of shapes and angles to force the weak eye into a proper position by exercising the lax muscles enough to maintain coordination or focus with the opposite or good eye. The ellipse configuration is made with "thumb" curves, short lines, longer lines, no right angles in the oval, and a wiggly line between two small squares.

In its preferred embodiment, the chart includes a peripheral line defining a geometric area or shape (preferably non-symmetrical) and a pair of intersecting lines bounded by the geometric area or shape (e.g., an oval). The intersecting lines are generally horizontal and vertical, although not mutually perpendicular, and divide the geometric shape into unequal quandrants. One of the intersecting lines can include a wavy portion. Marks such as arrows are superimposed on the intersecting lines where they abut the geometric shape. A number of images, preferably all of one shape, are superimposed on the geometric shape. Numerical figures of different sizes can be placed at various positions around the peripheral line and next to the intersecting lines. Images of a different shape can be placed outside the geometric shape to form part of a trapezoid.

The invention also encompasses methods for treating the eyes by exercises involving the eye chart. One such method includes the steps of placing an image, formed by the pair of intersecting lines of the chart, at a chosen distance from the eyes, positioning an object at a distance from the eyes parallel to one of the perpendicular lines and between the one line and the eyes, focusing the eyes on the object while moving the object progressively closer to the eyes, to thereby produce a double image of the one line and a single image of the other line, and maintaining the object in such position that it appears to lie between the respective portions of the double image.

The image also includes the peripheral line defining the geometric shape, and the method may further comprise the steps of moving the object in a path substantially within a plane between the image and the eyes and parallel to the plane of the image, at least a portion of the path corresponding in shape to the geometric shape, maintaining the object along a line between the eyes and a portion of the peripheral line, and continuously focusing the eyes on the object while moving the object through the path. At least a portion of the path may correspond to a chosen one of the intersecting lines. The method may further comprise the step of maintaining the object along a line between the eyes and a portion of the chosen perpendicular line while moving the object through the path.

Another method for treating the eyes in accordance with the invention includes the steps of following the peripheral line the chart with one eye while covering the other eye (e.g., with a hand) in a certain pattern. The image may include the pair of intersecting lines, and the method may further comprise the step of following at least one of the lines with one eye while covering the other (usually the better eye).

The image may further include the plurality of sub-images spaced along the peripheral line; and the method may further comprise the step of focusing upon one or more of the sub-images with one eye while covering the other. The method may also include the step of following the outline of at least one of the sub-images with at least one eye. Methods in accordance with the present invention may also be practiced with both eyes.

BRIEF DESCRIPTION OF THE DRAWING

The sole FIGURE depicts an embodiment of an eye chart in accordance with the present invention for use in treating amblyopia and diplopia. In the drawing FIGURE, one and two digit numerals form part of the eye chart of the invention. Three digit numbers are reference numbers provided for purposes of description only. The appended drawing FIGURE, while generally in the proper proportion, is smaller than the preferred size(s) described below and is not intended to be a substitute for the working chart.

DESCRIPTION OF A PREFERRED EMBODIMENT

Referring to the FIGURE, an eye chart 110 in accordance with the present invention includes a peripheral line 112 defining a geometric area or shape. As illustrated, the geometric area or shape is approximately oval or elliptical. It is to be understood that line 112 may define other shapes which may be non-symmetrical, such as an ellipse that is more bulbous at one end than the other.

Two intersecting lines, generally designated 114 and 116 penetrate into the geometric shape defined by peripheral line 112. As viewed in the drawing FIGURE, line 114 is generally vertical and line 116 is generally horizontal. It is to be understood that the designations horizontal and vertical are arbitrary; the chart can be oriented in various ways, as will be discussed below. Lines 114 and 116 preferably intersect at a slight angle from the perpendicular. In the illustrated embodiment, this angle S is approximately 89°. Line 114 includes a central wavy segment 114a extending outwardly from its intersection with and on either side of line 116, for a purpose to be described in greater detail below. Wavy segment 114a terminates in small solid blocks 118a and 118b. Straight line segments 114b and 114c extend from blocks 118a and 118b, respectively, to the point ends of arrows 122 and 124 respectively. Line 116 is composed of two segments 116a and 116b, which extend outwardly from the intersection of lines 114 and 116 to the point ends of arrows 126 and 128, respectively. Lines 114 and 116 divide ellipse 112 into four quadrants. For purposes of the present description, these are designated: upper left quadrant (I), lower left quadrant (II), upper right quadrant (III), and lower right quadrant (IV).

In the embodiment shown, the ellipse defined by peripheral line 112 is asymmetric. Lines 114 and 116 do not intersect at their respective midpoints. Line segment 114i is longer than line segment 114b; and line segment 116b is approximately equal in length to line segment 116a. As a result, the curve of peripheral line 112 in upper and lower right quadrants III and IV is rounder than the curve of peripheral line 112 in upper and lower left quadrants I and II. Quadrents I-IV have unequal areas. The irregular shape coaxes the weaker eye into the proper position during exercises using the chart.

Arrows 122 and 124 are superimposed on line segments 114b and 114c, respectively. Arrows 126 and 128 are superimposed on line segments 116a and 116b, respectively. All of arrows 122-128 extends outside ellipse 112 to draw the eye onto the ellipse along lines 114 and 116. In a preferred embodiment arrows 122, 124, and 126 are solid, and arrow 128 is depicted in outline.

A number of images 130 are superimposed on ellipse 112 spaced apart from one another. In one preferred embodiment, the images 130 are in the shape of spools or dumbbells. Other shapes, such as diamonds and hearts may also be used. In the embodiment illustrated, there are seventy spools or dumbbells 130. Four spools 130a, 130b, 130c, and 130d are superimposed on arrows 122, 124, 126, and 128, respectively. The remaining sixty-six spools are spaced approximately evenly along line 112. In the embodiment shown, sixteen spools are spaced along the segments of line 112 in each of quadrants III and IV; seventeen spools are spaced along the segments of line 112 in each of quadrants I and II. Sixty-eight of the spools 130 are substantially identical in size. The sixty-ninth spool is more elongated and the seventieth spool is shorter than the other sixty-eight. As illustrated, spool 130a is the shorter spool and spool 130b is the elongated spool. However, the positions of the shorter and longer spools are arbitrary, and they can be located at any point on ellipse 112.

A plurality of sub-images, generally designated 132 and preferably in the shape of dumbbells (although other shapes may be used), is placed outside peripheral line 112 to form the corners of an open box around elliptical shape 112. In the preferred embodiment illustrated, there are twenty dumbbells 132 arranged in groups of five to form the corners of a geometric shape which is approximately rectangular. For ease of reference, the several groups are designated here by the letters A, B, C, D. Each group of dumbbells 132 is made up of a row 132a of three dumbbells and a row 132b of two dumbbells at an angle to each other. Rows 132a and 132b of each of groups A and B are at right angles to each other. The rows 132a of three dumbbells are approximately even with spools 130a and 130b, while the rows 132b of two dumbbells are approximately even with spools 130c and 130d. Rows 132a and 132b of each of groups C and D form acute angles slightly less than 90°. This non-symmetrical arrangement of dumbbells 132 draws the eyes into and around ellipse 112.

There are thirteen numbers of three different sizes arranged on the chart for a purpose to be described below. There are four large numbers, placed outside ellipse 112: the number "17" immediately to the right of arrow 122; the number "19" immediately below arrow 124; the number "21" immediately above arrow 126; and the number "23" immediately below arrow 128. There are five medium-sized numbers: the number "7" placed immediately outside ellipse 112 at upper left quadrant I; the number "9" immediately inside ellipse 112 in upper left quadrant I; the number "11" to the right of line segment 114b below arrow 122; the number "13" immediately above line segment 116 to the left of arrow 128; and the number "25" immediately inside ellipse 112 in lower left quadrant II. The remaining four numbers are the smallest: the numbers "15" and "27" are located in quadrants II and III, respectively, adjacent the intersection of lines 114 and 116; the number "29" is located immediately to the left of square 118a; and the number "31" is located immediately to the left of square 118b. It should be understood that the numbers used are arbitrary, and that other numbers can be chosen as desired.

A chart according to the present invention, designed for viewing at an optimum range of 2-3 feet, would have vertical line 114 approximately $6\frac{3}{4}$ inches long and a horizontal line 116 approximately 11½ inches long. For viewing at greater distances, the size of ellipse 112, vertical line 114, horizontal line 116, spools 130, dumbbells 132, and the numbers can be increased proportionally, preferably maintaining a ratio of ellipse height to width of about 1:1.7. A very large chart having an ellipse 112 as wide as ten feet can be placed on the ceiling.

The chart can be printed in black on a white background, in several colors on a background of a different color, or in different shades of the same color. Shadows can be incorporated to give arrows 122–128, images 130, images 132, and the numbers a three-dimensional appearance.

DESCRIPTION OF METHOD OF USING THE INVENTION

In use, the chart may be hung vertically, for example on a wall, with line 116 approximately horizontal and at eye level. Alternatively, the chart may be mounted to a relatively rigid backing, such as cardboard, and propped on a table in any known manner. It can then be turned each day to vary the exercises. The user preferably stands 2-3 feet away from the chart, or closer if necessary to see clearly. It is better to do the exercises without glasses, but glasses can be worn, if necessary.

There are a number of exercises which can be performed using the chart. Each exercise should be repeated five times, several times a day. The chart should then be turned 90°, and the exercise repeated five more times. This sequence is followed until the chart is returned to its original position. Rest periods should be taken between repetitions if the eyes become tired. The exercises should be done slowly at first, speeding up as improvement of the eyes takes place. Obviously, it is desirable to repeat the exercises more often with the weaker eye (covering the better eye) so that the muscles associated therewith may be strengthened to the greatest degree possible.

As a preliminary exercise, the user should count the wide spaces between the images on the oval. Thereafter, the narrow spaces should be counted. Other specific exercises are described below.

EXERCISE 1

An object, such as a ballpoint pen with a shiny point, is held at arm's length in visual alignment with the vertical line 14. Both eyes are focused on the object (e.g., the pen point). With the eyes focused on the pen point, the pen is brought slowly towards the eyes. Side vision will cause the ellipse 112 to appear as two ellipses overlapping each other. A double image of the vertical line 114 will appear. The pen should be kept between the two images. Horizontal line 116 will remain a single image. The pen is stopped (or carried to the nose) when the double image of the ellipse 112 and the vertical line 114 are clearly visible. The pen is held in this position for a count of five. If the image fades before the count is finished, the process should be repeated after a brief rest. The exercise can be reversed by starting from the nose and reversing the above-described steps.

As a variation of this exercise, when the double image of the ellipse 112 and the vertical line 114 are clearly visible, the eyes are closed. When they are reopened, the eyes are focused on the pen point. This process should be repeated until the ellipse and the vertical lines appear double when the eyes are reopened. The eyes should remain focused on the pen point for a count of five. The pen is then moved back to arm's length. When the pen is back at arm's length, the single ellipse should reappear.

A narrow vertical island also appears in the center when the chart is hung vertically. The user of the chart may find at first that the island is wide at the center. After diligent use and exercise, however, the user should find that the island will become much narrower. The narrowing island shows that progress is being made.

Arrows 122, 124, 126 and 128 associated with lines 114 and 116, respectively, may be used to gauge one's progress. Assuming that line 114 is horizontally oriented, when a double image of the chart appears, as described above, arrows 122 and 124 will appear to move toward each other. The apparent distance between arrows 122 and 124 may be used as an indication of the degree of progress which one has made. As the eye muscles are strengthened, the individual will be able to make arrows 122 and 124 move closer and closer together. This is, of course, applicable to arrows 126 and 128 also, assuming that line 114 is oriented horizontally.

EXERCISE 2

A pen with a shiny point is held at arm's length and one eye is closed. The pen point is used to trace the shape of the ellipse 112. The open eye follows the pen point. When the left eye is open, the ellipse 112 is traced clockwise. When the right eye is open, the ellipse 112 is traced counterclockwise. When the chart is used by children, for example, it may be best to cover the better eye (e.g., with the hand).

Next, both eyes are opened, and the ellipse 112 is traced clockwise, then counterclockwise.

After the ellipse 112 has been traced with each eye alone and both eyes together, the pen point is used to trace the vertical and horizontal lines 114 and 116, including the wavy line segment 114a. The lines are traced first with one eye, then with the other eye, and then with both eyes.

EXERCISE 3

With the head held fixed, the eyes are forced to follow the vertical and horizontal lines 114 and 116 up and down and side-to-side, respectively. This is repeated five times.

Next, with the head moving and the eyes held rigid, the vertical and horizontal lines 114 and 116 are traced up and down and side-to-side, respectively. This also is repeated five times.

EXERCISE 4

Starting at the top of the ellipse 112 and going all the way around, the spools 130 are be counted. Alternatively, the spools can be counted starting at the top of the ellipse 112 and stopping at the top spool 130a or the bottom spool 130b. The horizontal line 116 is then followed to the other side of the ellipse 112, and counting the spools is continued either clockwise or counterclockwise around the ellipse 112. After the spools 130 are counted, the dumbbells 132 are counted.

After the chart has been used for some time, this exercise can be varied by stopping at any spool 130 and, with one eye closed, tracing its outline. The counting is then continued until a quarter of the way around the ellipse 112. Again, counting is stopped and with one eye closed, another spool 130 is traced. This pattern is continued until a number of spools can be traced successively without becoming blurred or fuzzy.

EXERCISE 5

One eye is closed (or covered). The open eye weaves back and forth through the spools 130 around the ellipse 112.

EXERCISE 6

The stronger eye is closed (or covered). With the weak eye, the ellipse 112 is entered at the top arrow 122. It travels clockwise along the ellipse 112 to right arrow 128. Here, the weak eye traces the number "23". The weak eye then continues clockwise following the ellipse 112 to the bottom arrow 124. Here, the weak eye traces the number "19". These steps are continued until the weak eye returns to the number "17"; then the process is repeated in reverse, the weak eye traveling counterclockwise.

EXERCISE 7

After becoming familiar with the chart, the user should cover the good eye (e.g., with the hand) and count the images two at a time around the oval in one direction. The direction of counting should then be reversed.

Next, the numbers "7", "9", and "25" are traced, followed by the numbers "11", "13", "15", "27", "29" and "31". When the chart is rotated, the numbers are traced sideways or upside down, depending upon the position of the chart.

The various exercises may be repeated with chart 110 positioned upside-down or in such manner that line 116 is vertically oriented, with either the left or right side of the chart at the top. In various positions, the degree of eye movement in the several directions necessary to follow various portions of peripheral line 112 is altered due to the bulges and variations in the curve defining the shape of the chart. This varies the strain imposed on the eye muscles as the eye is moved up, down and side-to-side.

Dumbbell-shaped sub-images 132 may be used in other exercises adapted to improve one's control over the eye muscles. Using both eyes, or preferably the weaker eye along, the individual should count dumbbells many times, focusing the eye or eyes successively on individual images 132. The outline of individual images 132 may be traced with the weaker eye or both eyes, thus improving muscular control. It is advisable to trace the line of images 132 at various locations on peripheral line 112, thus improving control over the eye while it is pointed in various directions. One may also follow a visual path around the chart, slowly weaving in and out between images 132. This can be done variously by moving the head or by keeping the head still (except when using the larger charts) and moving the eyes.

Wavy segment 114a of line 114 may also be usd to exercise the muscles associated with either or both eyes. One may attempt to follow the wavy configuration of line segment 114a with the weaker eye or eyes, thus improving muscular control. Due to the small size of the angular deviations in wavy line segment 114a, it requires very accurate control of the eye to actually trace the path of wavy segment 114a. Thus, an ability to follow the path of segment 114a between the points 118a and 118b is indicative of significant progress in rehabilitation of the eye muscles.

Amblyopia and diplopia are conditions which often occur in relatively young children. It would of course be desirable for these children to exercise their eyes in the manner described above. The configuration of a chart in accordance with the present invention lends itself to making a game of the required exercises.

These exercises can be used by persons of all ages, even relatively young children. When the chart is used by a child, it can be described as, for example, a tennis or volleyball court. The entrance to the "court" would be through arrow 23. The wavy portion 114a, between squares 118a and 118b, represents the net hung on a pair of poles. Spools 130 represent benches. The child can be told to follow an imaginary vollyball or tennis ball back and forth across the net between various points along the horizontal line 116. The child can be asked to pretend that he or she is trying to spot a friend sitting on one of the benches, therefore focusing on individual spools 130 or dumbbells 132. Each bench can be searched carefully by tracing its outline with the one eye while covering the other eye.

A large chart placed on the ceiling is intended for use by a person who is lying down. Ideally, the person should be on a couch, bed or reclining chair that can be rotated.

The longer a person has had amblyopia or diplopia, the longer it will take to correct the problem. Thus, an older person generally will have to use the chart longer than a younger person.

After the chart has been used for a while, the individual will be able to invent variations on the exercises and to device additional exercises. Variations and new exercises should be done in the same manner as the exercises described here, slowly at first and then faster, repeating each exercise five times, and rotating the chart.

While the invention has been disclosed with reference to the accompanying Figure, neither the chart nor the method of the present invention should be construed as limited to the details disclosed herein, as the disclosed embodiment is merely illustrative of the inveniton, the scope of the invention being limited only by the claims appended hereto.

I claim as my invention:

1. An eye exercise chart, comprising:
   (a) a background of opaque material;
   (b) a peripheral line formed on the background, wherein
      (i) the peripheral line defines a nonsymmetric, substantially elliptical shape;
      (ii) the lack of symmetry is visually detectable; and
      (iii) a plurality of target images are superimposed on and along the peripheral line;
   (c) a pair of intersecting lines approximately perpendicular to each other formed on the background within the area defined by the peripheral line, at least one of the intersecting lines including an intermediate, wavy portion;
   wherein said intersecting lines abut said peripheral line and divide said area into four sections;
   wherein markers are superimposed over said intersecting lines where said intersecting lines abut said peripheral line; and
   wherein a plurality of spool-shaped images are superimposed and are substantially evenly spaced along said peripheral line, one of said spool-shaped images is shorter than the others, another one of said spool-shaped images is longer than the others, and the other spool-shaped images are substantially the same size.

2. A chart as in claim 1, wherein said markers extend outside said peripheral line, and are arrow-shaped with tapered ends pointing into the geometric area defined by said peripheral line.

3. A chart as in claim 1, wherein numerals are placed inside and outside said peripheral line.

4. A chart as in claim 1, wherein a plurality of images are placed outside said peripheral line.

5. A chart as in claim 4, wherein said images are dumbbell-shaped.

6. A chart as in claim 5, wherein said dumbbell-shaped images form the corners of a second geometric shape which is approximately rectangular.

7. An eye chart according to claim 1 wherein two of said sections located on the same side of one of said intersecting lines have areas that are greater than the areas of the two sections located on the opposite side of said one line.

8. A method for treating the eyes comprising:
placing a chart having a peripheral line defining a geometric shape and a pair of intersecting lines contained in said geometric shape, one of said lines being generally vertical, at a chosen distance from the eyes;
positioning an object at a distance from the eyes parallel to said generally vertical line and between the chart and the eyes;
focusing the eyes on the object while moving the object progressively closer to the eyes, resulting in a double image of said generally vertical line; and
maintaining the object in such position that it appears to lie between the respective portions of the double image.

9. A method as in claim 8, further comprising the steps of:
moving the object in a path substantially within a plane between the image and the eyes and parallel to the plane of the image, at least a portion of said path corresponding in shape to the geometric shape, while maintaining the object along a line between the eyes and a portion of said peripheral line; and
continuously focussing the eyes on the object while moving the object through said path.

10. A method as in claim 9, wherein at least a portion of said path corresponds to at least a chosen one of the intersecting lines, the method further comprising the step of maintaining the object along a line between the eyes and a portion of the chosen intersecting line while moving the object through said path.

11. A method as in claim 8, in which the chart further includes a plurality of shapes spaced along the peripheral line, said method further comprising the step of sequentially focusing on one or more of the shapes with at least one eye.

12. A method as in claim 11, further comprising the step of following the outline of at least one of the shapes with at least one eye.

13. A method as in claim 12, wherein said method is performed using both eyes.

14. An eye exercise chart, comprising:
(a) a background of opaque material;
(b) a peripheral line formed on the background, wherein the peripheral line defines a visibly non-symmetric, substantially elliptical shape;
(c) a pair of intersecting lines formed on the background within the area defined by the peripheral line, wherein the intersecting lines are approximately perpendicular and divide the area into four sections having visibly unequal areas;
(d) a plurality of images superimposed along the peripheral line, wherein the images are substantially evenly placed along the peripheral line, one of the images is visibly shorter than the others, one of the images is visibly longer than the others, and the other images are substantially the same size; and
(e) a plurality of images placed outside of the peripheral line, wherein the images form the corners of a second geometric shape which is approximately rectangular and visibly non-symmetric.

15. An eye exercise chart, comprising: a peripheral line defining a non-symmetric, substantially elliptical shape, wherein the lack of symmetry is visually detectable; a plurality of substantially similar target images superimposed on and along the peripheral line; and a pair of intersecting lines approximately perpendicular to each other formed within the area defined by the peripheral line, at least one of the intersecting lines including an intermediate, wavy portion:
wherein said target images are spool-shaped and are substantially evenly spaced along said peripheral line, one of said spool-shaped images being shorter than the others, another one of said spool-shaped images being longer than the others, and the remaining spool-shaped images being substantially the same size.

16. A chart as in claim 15, wherein said intersecting lines abut said peripheral line and divide said area into four sections.

17. A chart as in claim 16, wherein said sections have unequal areas.

18. A chart as in claim 16, wherein markers are superimposed over said intersecting lines where said intersecting lines abut said peripheral line.

19. A chart as in claim 18, wherein said markers extend outside said peripheral line, and are arrow-shaped with tapered ends pointing into the geometric area defined by said peripheral line.

20. An eye exercise chart, comprising:
a peripheral line defining a visibly non-symmetric, substantially ellipical shape;
a pair of intersecting lines formed within the area defined by the peripheral line, wherein the intersecting lines are approximately perpendicular and divide the area into four sections having visibly unequal areas;
a plurality of images superimposed along the peripheral line, wherein the images are substantially evenly placed along the peripheral line, one of the images is visibly shorter than the others, one of the images is visibly longer than the others, and the other images are substantially the same size; and
a plurality of images placed outside of the peripheral line, wherein the images form the corners of a second geometric shape which is approximately rectangular and visibly non-symmetric.

* * * * *